United States Patent [19]

Nickson

[11] Patent Number: 4,503,276

[45] Date of Patent: Mar. 5, 1985

[54] PROCESS FOR SEPARATING NITRATION ISOMERS OF SUBSTITUTED BENZENE COMPOUNDS

[75] Inventor: Thomas E. Nickson, St. Charles, Mo.

[73] Assignee: Monsanto Company, St. Louis, Mo.

[21] Appl. No.: 569,065

[22] Filed: Jan. 9, 1984

[51] Int. Cl.³ .............................................. C07C 79/12
[52] U.S. Cl. ................................. 568/936; 260/505 P; 560/20; 562/494; 568/30; 568/306; 568/424; 568/937
[58] Field of Search ....................... 260/505 P; 560/20; 562/494; 568/30, 306, 424, 936, 937

[56] References Cited

U.S. PATENT DOCUMENTS 4,242,286 12/1980 Ohsaka ............................ 568/936 X

OTHER PUBLICATIONS

ARCAS, Chem. Abs., vol. 99, 194603m, Dec. 5, 1983.

*Primary Examiner*—Leland A. Sebastian
*Attorney, Agent, or Firm*—Robert B. Martin; Richard H. Shear

[57] ABSTRACT

This invention pertains to a process for separating nitration isomers of 1,3-disubstituted and 1,2,4-trisubstituted benzene compounds. The separated isomers have a variety of uses including precursors for 2-haloacetanilide herbicides.

5 Claims, No Drawings

PROCESS FOR SEPARATING NITRATION ISOMERS OF SUBSTITUTED BENZENE COMPOUNDS

FIELD OF THE INVENTION

The invention herein pertains to a process for separating nitration isomers of substituted benzene compounds. The separated isomers have a variety of uses including precursors for 2-haloacetanilide herbicides.

BACKGROUND OF THE INVENTION

Generally, it is difficult to separate positional nitration isomers of aromatic compounds utilizing variations in physical properties. For example, generally it is difficult to separate nitration isomers of substituted benzene compounds using physical means, such as distillation, chromotography, etc. Although these techniques can generally be utilized in a laboratory to isolate each positional isomer in relatively pure form, they are normally uneconomical in a commercial setting.

It is an object of the present invention to provide a new process for separating nitration isomers of substituted benzene compounds.

Other objects and advantages will become apparent from the following disclosure.

SUMMARY OF THE INVENTION

The present invention relates to a new process for separating the hindered nitration isomer from a mixture of hindered and unhindered nitration isomers obtained from the mononitration of disubstituted and trisubstituted benzene compounds. The hindered nitration isomer separated by the process of the present invention is useful as precursor for the preparation of 2-haloacetanilide herbicides. Generally, standard laboratory nitration of 1,3-disubstituted benzene compounds and 1,2,4-trisubstituted benzene compounds having an open hindered position on the ring will result in the formation of a mixture of both hindered and unhindered nitration isomers. Frequently, these isomers will have remarkably similar physical properties making it difficult to separate them by art known techniques. The process of the present invention enables separation of the hindered nitration isomer from unhindered nitration isomers. The process of the present invention generally comprises the steps of (a) mixing a nonorganic sulfide salt with the mixture of hindered and unhindered mononitration isomers of a substituted benzene to reduce substantially all of the unhindered nitration isomers with no reduction of substantially all of the hindered nitration isomer, and (b) separating the reduced isomers from the hindered nitration isomer.

The separation of the isomers from each other after reduction can be accomplished using standard laboratory techniques which rely on differences in physical or chemical properties between the nitro and amino substituted benzene compounds. Conveniently, the separation may be accomplished utilizing standard acid-base extraction techniques.

A more thorough disclosure of the present invention is presented in the detailed description which follows.

DETAILED DESCRIPTION OF THE INVENTION

The present invention relates to a new process for separating the hindered nitration isomer from a mixture of hindered and unhindered nitration isomers obtained from the mononitration of 1,3-disubstituted and 1,2,4-trisubstituted benzene compounds. Generally, standard laboratory nitration of meta-disubstituted benzene compounds and trisubstituted benzene compounds having an open hindered position on the ring will result in the formation of a mixture of both hindered and unhindered nitration isomers. A hindered nitration isomer has two adjacent substituents such as 2-nitro-1,3-disubstituted benzene. The process of the present invention generally comprises a process for separating the compound having the formula:

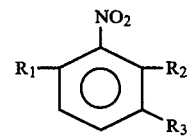

from a mixture of hindered and unhindered mononitration isomers having the formula:

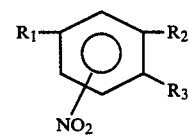

comprising the steps of:
(a) mixing a nonorganic sulfide salt with the mixture to reduce substantially all of the unhindered nitration isomers in the mixture with no reduction of substantially all of the hindered nitration isomer; and
(b) separating the reduced isomers from the hindered nitration isomer;
wherein in the above formula $R_1$ and $R_2$ are independently lower ($C_1$-$C_4$) alkyl, $CF_3$, alkanoyl, carboxyl, aryl, halogen, alkyl-sulfone, or sulfo, and $R_3$ is independently hydrogen, lower ($C_1$-$C_4$) alkyl, $CF_3$, alkanoyl, carboxyl, aryl, sulfo, alkyl-sulfone, or halogen.

The reduction can be generally represented as follows:

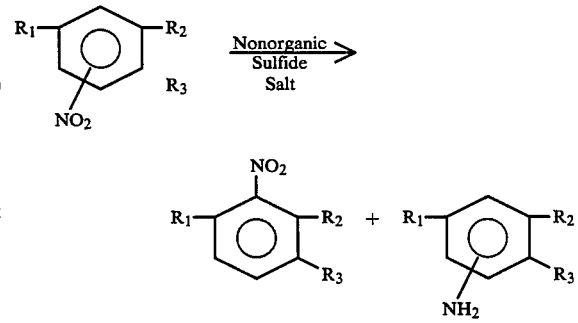

A variety of substituted benzene compounds can be utilized to form the nitration mixture used in the process of the present invention provided that the substituents do not interfere with the process of the invention. Highly activating substituents which donate electron density to the benzene ring should be avoided because they inhibit the reduction of the nitro group. Also, substituents which are easily oxidized or are subject to nucleophilic attack should be avoided. Convenient substituents are lower ($C_1$–$C_4$) alkyl, $CF_3$, and halogen. A preferred subgenus of substituents are lower ($C_1$–$C_2$) alkyl, trifluoromethyl, and halogen. Preferred starting compounds for forming the nitration mixture used in the process of the present invention are 3-methylbenzotrifluoride and 3-ethylbenzotrifluoride.

As used herein, the term "alkyl" refers to both straight chain and branched chain alkyl radicals, preferred are alkyls containing 1 to 3 carbon atoms such as methyl, ethyl, n-propyl, and isopropyl; "aryl" refers to aromatic radicals; "alkanoyl", "carboxyl", and "alkylsulfone" refer to radicals of the formula —COR, —COOR, and —SO₂R, respectively, where R is hydrogen, alkyl, or aryl; and "sulfo" refers to $SO_3H$.

Methods for making the preferred starting compounds for the present invention are set forth in the chemical literature. The 3-methyl benzotrifluoride can be prepared according to the procedures set forth in JACS 65 389 (1943) or Chem. Letters 1719 (1981). The 3-methylbenzotrifluoride can also be prepared by reduction by standard laboratory procedures of commercially available 3-chloromethylbenzotrifluoride or 3-trifluoromethyl benzaldehyde or 3-dichloromethyl benzotrifluoride prepared in accordance with U.S. Pat. No. 4,367,348 or J. Org. Chem. 43 1071 (1978). The 3-ethylbenzotrifluuoride can be prepared by reduction of commercially available m-trifluoromethyl acetophenone following known laboratory procedures.

The nitration of the substituted benzene compounds can be accomplished using standard laboratory procedures. Conveniently, the substituted benzene compound can be nitrated with a suitable nitrating agent, such as nitric acid, oxides of nitrogen, e.g., dinitrogen pentoxide or nitronium tetrafluoroborate. If desired, the nitration can be accomplished in an inert organic solvent, such as 1,2 dichloroethane, with a suitable acid cosolvent, such as sulfuric acid. After the nitration reaction, the product is isolated by standard laboratory procedures.

Generally, the nitration of a 1,3-disubstituted benzene compound will result in the formation of a mixture of the 2-, 4-, 5- and 6-nitro isomers of the 1,3-disubstituted benzene compound. For example, nitration of 3-methylbenzotrifluoride with concentrated nitric acid at a temperature of about 5° C. results in the following nitro isomer distribution: 2- (44%); 4- (21%); 5- (2%); and 6-(33%). These nitration isomers have remarkably similar physical properties which makes their separation difficult. The process of the present invention enables separation of the hindered 2-nitro isomer from the other unhindered nitration isomers.

In the first step of the process of the present invention, the mixture of the nitration isomers of the substituted benzene compound is combined with a nonorganic sulfide salt to reduce all of the unhindered nitro substituents to amino substituents, such as substantially all of the 4-, 5- and 6-nitro isomers of the 1,3-disubstituted benzene, without reduction of substantially all of the hindered nitro isomer, such as the 2-nitro isomer of the 1,3-disubstituted benzene.

A variety of nonorganic sulfide salts may be used in the process of the present invention. Nonorganic sulfide salts are inorganic sulfide salts which do not contain carbon. Nonorganic sulfide salts include mono-, di-, and polysulfides and sulfhydrates. Suitable sulfide salts are ammonium, sodium, or potassium sulfide, hydrosulfides or polysulfides, manganous sulfide, zinc sulfide, and ferrous sulfides and hydrates thereof. The sodium and ammonium sulfide salts are preferred because of their solubility and commercial availability. Conveniently, sulfur is added to the reaction mixture. Alternatively, the sulfide salt can be generated in situ with sodium hydroxide and hydrogen sulfide.

The mixture of mononitration isomers of a substituted benzene are combined with the nonorganic sulfide salt in a suitable reaction vessel. The sulfide salt is preferably added to the nitration mixture to avoid side reactions. Preferably about 1.0 to about 6.0 moles of sulfide salt are added per mole of nitration mixture. Greater amounts of salt will increase the rate of reaction. The reduction is conveniently accomplished in an inert solvent, such as aqueous alcohol.

During the reaction, the pH of the reaction mixture will fall with the formation of thiosulfate and the rate of the reaction will slow down. In some cases it may be desirable to add base during the reaction to maintain the rate of the reaction at a reasonable rate. Suitable bases are alkali and alkaline earth metal oxides and hydroxides and ammonium hydroxide. A convenient base is sodium hydroxide. Other bases which can be used in the process of the present invention will be known to those skilled in the art.

In some cases, the substituents on the benzene may be susceptible to side reactions during the reduction. For example, the trifluoromethyl substituent is susceptible to hydrolysis at higher pH. Therefore, if one of the substituents is susceptible to side reactions, it is desirable to maintain the pH of the reaction mixture preferably within the range of about 10 to about 13 and more preferably from about 11 to about 12. Lower pH will slow the reaction rate and higher pH may result in side reactions of the substituents, such as hydrolysis.

Upon the addition of the sulfide salt to the reaction mixture, the pH of the reaction mixture may, in some cases, exceed 13. Therefore, in some cases, e.g., for trifluoromethyl substituted benzenes, it is desirable to add a buffer to the reaction mixture to inhibit side reactions. Suitable buffers are ammonium chloride, sodium bicarbonate, and triethyl amine hydrochloride. Other buffers which can be used in the process of the present invention will be known to those skilled in the art.

The reaction may be conveniently run at a temperature from about 50° C. to about 100° C. After addition of the sulfide salt to the reaction mixture, the mixture is stirred for a period of about 3 to about 6 hours. The reaction will generally result in reduction of about 97% of the unhindered nitro substituents to amino substituents and in reduction of only about 0.5% to 1% of the hindered nitro substituent to an amino substituent.

Upon completion of the reduction, the nitro substituted benzene can be conveniently separated from amino substituted benzene by standard laboratory separation techniques which rely on differences in physical properties between amino and nitro substituted benzene compounds. Suitable separation techniques include acid-base extraction, distillation, chromatography, and fractional crystallization. Conveniently, a sufficient amount of acid, such as mineral acid, is added to form the corresponding anilinium salt. The completion of the salt formation can be detected by the presence of excess acid or gc.

The isolated nitro substituted benzene may then be reduced to form the corresponding aniline. These anilines are precursors for various 2-haloacetanilide herbicides. The aniline may be formed by hydrogenating the nitro substituted benzene. Conveniently, the nitro substituted benzene is dissolved in a suitable solvent, such as polar solvents, e.g., aqueous alcohols. The reaction mixture also conveniently includes a hydrogenation catalyst, such as palladium on carbon or Raney nickel. These reagents are conveniently combined in a suitable vessel. The hydrogenation reaction can be carried out at any suitable hydrogen pressure from atmospheric to about 61 atmospheres ($61.8 \times 10^5$ pascals), preferably from about 3.4–13.6 atmospheres ($3.44$–$13.77 \times 10^5$ pascals). After reduction, the precursor aniline can be isolated using standard laboratory techniques.

The precursor anilines can then be converted to various 2-haloacetanilide by a variety of methods. For example, tertiary 2-haloacetanilide can be prepared by haloacetylation of the precursor aniline by known procedures to form a secondary 2-haloacetanilide which is then N-alkylated to form 2-haloacetanilide herbicides. The haloacetylation of the aniline can be accomplished by adding a slight molar excess of chloroacetyl chloride to the aniline in a suitable organic solvent, such as chlorobenzene, and heating the solution to reflux for a short period of time. The secondary 2-haloacetanilide is then N-alkylated according to known procedures.

An N-alkylation process is described in detail in U.S. Pat. No. 4,258,196. A modified N-alkylation process is described in U.S. Pat. No. 4,284,564. The 2-haloacetanilides may also be made by a transetherification process. This process is described in U.S. Pat. No. 4,296,254. Tertiary 2-haloacetanilides may also be prepared from the precursor aniline in accordance with the procedures disclosed in Belgium Pat. No. 887,997. These patents are incorporated herein by reference.

The following examples are presented to illustrate the present invention as well as some of the various embodiments of the invention. These examples are presented as being illustrative of the novel process of the invention and are not intended to be a limitation as to the scope thereof.

EXAMPLE I

2-Nitro-3-Methylbenzotrifluoride

A 500 ml flask was charged with 175 ml of 2M $Na_2S$ (0.35 mole) in 1:1 ethanol:$H_2O$ followed by addition of 13.8 gms of sublimed sulfur (0.4 mole). The resultant mixture was diluted with 125 ml of 4:1 ethanol:$H_2O$. After 1 hour at room temperature, 9.4 gms (0.175 mole) of $NH_4Cl$ was added and stirred for 15 minutes and the mixture was subsequently transferred to an additional funnel. The $Na_2S_2/NH_4Cl$ solution was then added slowly to 41 gms (0.2 mole) of a mixture of nitration isomers dissolved in 100 ml of 1:1 water:ethanol at 75° C. The mixture of nitration isomers was obtained by nitration of 3-methylbenzotrifluoride. The mixture comprised 44% of the 2-isomer, 34% of the 6-isomer, 20% of the 4-isomer, and 2% of the 5-isomer. After a brief exotherm the reaction slowed down and caustic was added (25% NaOH) periodically to keep the pH at 11–12. After 5 hours at 75° C. the reaction was complete, and the mixture was allowed to cool to room temperature. The final mixture was diluted with 500 ml of $H_2O$ and extracted 3 times with 100 mls of $CH_2Cl_2$. The $CH_2Cl_2$ layers were combined and treated with gaseous HCl until all the anilinium hydrochlorides had precipitated. Filtration followed by concentration gave 17.1 gms (95% yield) of solid 2-nitro-3-methylbenzotrifluoride. b.p. 48°–49° C. (at 0.1 mm/Hg).

EXAMPLE II

2-Nitro-3-Methylbenzotrifluoride

At 60° C., 84.0 gms (0.35 mole) of $Na_2S$ $9H_2O$ was mixed with 13.8 gms (0.4 mole) of sulfur in 200 ml MeOH and 100 ml $H_2O$. After all the solids had dissolved (about 1 hour) 4.7 gms (0.0875 moles) of $NH_4Cl$ was added and stirred for 15 minutes. The temperature was brought to 75° C. and 57.4 gms (0.28 mole) of the nitro-mixture of Example I was slowly added over a 20 minute period. After 30 minutes sodium hydroxide was periodically added to maintain a pH of 11–12. The reaction required 5 hours to complete and then it was cooled, diluted with 500 ml $H_2O$, and extracted 3 times with $CH_2Cl_2$ (100 ml aliquates). The $CH_2Cl_2$ was then mixed with 40 gms of 96% $H_2SO_4$. The two layers were stirred rapidly for 1 hour and separated. Concentration of the organic layer gave 23.5 gms (93% yield) of 2-nitro-3-methylbenzotrifluoride.

EXAMPLE III

2-Nitro-3-Methyl-6-Chloro Benzotrifluoride

In 2 ml of methanol, 0.7 gms (3.1 m moles) of a mixture of nitration isomers of 3-methyl-6-chloro benzotrifluoride (2-nitro-29%; 4-nitro-8%; 5-nitro-62%) was treated with 12 m moles of $(NH_4)_2S_x$ in $H_2O$ at 65° C. A vigorous exotherm ensued and the reaction was heated for 2 hours. The final dark mixture was cooled to room temperature, diluted with 10 mls $H_2O$ and extracted twice with 5 mls $CH_2Cl_2$. The mixture was then extracted with 10% HCl to remove the reduced anilines. GC/ms (GC retention time and M+229) verified that the 2-nitro isomer was the only nitro isomer.

Although this invention has been described with respect to specific embodiments, the details thereof are not to be construed as limitations, for it will be apparent that various embodiments, changes, and modifications may be resorted to without departing from the spirit and scope thereof and it is understood that such equivalent embodiments are intended to be included within the scope of this invention.

I claim:

1. A process for separating the compound having the formula:

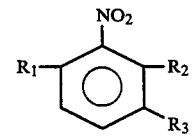

from a mixture of hindered and unhindered nitration isomers having the formula:

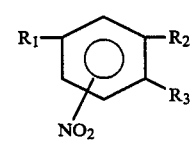

comprising the steps of:
(a) mixing a nonorganic sulfide salt with the mixture to reduce substantially all of the unhindered nitration isomers in the mixture with no reduction of substantially all of the hindered nitration isomer; and (b) separating the reduced isomers from the hindered nitration isomer;

wherein in the above formula $R_1$ and $R_2$ are independently lower ($C_1$–$C_4$) alkyl, $CF_3$, alkanoyl, carboxyl, aryl, sulfo, alkyl-sulfone, or halogen, and $R_3$ is independently hydrogen, lower ($C_1$–$C_4$) alkyl, $CF_3$, alkanoyl, carboxyl, aryl, sulfo, alkyl-sulfone, or halogen.

2. The process of claim 1 wherein $R_1$ and $R_2$ are independently $C_1$–$C_2$ alkyl, trifluoromethyl, or halogen, and $R_3$ is hydrogen.

3. The process of claim 1 wherein $R_1$ is methyl, $R_2$ is trifluoromethyl, and $R_3$ is hydrogen.

4. The process of claim 1 wherein $R_1$ is ethyl, $R_2$ is trifluoromethyl, and $R_3$ is hydrogen.

5. The process of claim 1 wherein the nonorganic sulfide salt is selected from the group consisting of sodium and ammonium sulfides.

* * * * *